United States Patent [19]

Rose et al.

[11] E Re. 30,199

[45] Reissued Jan. 29, 1980

[54] OXIDATION HAIR DYES BASED UPON TETRAAMINOPYRIMIDINE DEVELOPERS

[75] Inventors: David Rose, Düsseldorf-Holthausen; Ferdi Saygin, Erkrath; Erwin Weinrich, Düsseldorf-Holthausen, all of Fed. Rep. of Germany

[73] Assignee: Henkel Kommanditgesellschaft auf Aktien (Henkel KGaA), Düsseldorf-Holthausen, Fed. Rep. of Germany

[21] Appl. No.: 953,688

[22] Filed: Oct. 23, 1978

Related U.S. Patent Documents

Reissue of:

[64] Patent No.: 4,003,699
Issued: Jan. 18, 1977
Appl. No.: 526,232
Filed: Nov. 22, 1974

[30] Foreign Application Priority Data

Nov. 29, 1973 [DE] Fed. Rep. of Germany ..... 2359399
Oct. 2, 1974 [DE] Fed. Rep. of Germany ..... 2447017

[51] Int. Cl.[2] ..... A61K 7/13

[52] U.S. Cl. ..... 8/10.2; 8/11; 8/32

[58] Field of Search ..... 8/10.2, 11, 32

[56] References Cited

U.S. PATENT DOCUMENTS

| | | | |
|---|---|---|---|
| 2,350,812 | 6/1944 | Peterson | 96/56.5 |
| 2,355,691 | 8/1944 | Allen et al. | 96/56.5 |
| 3,359,168 | 12/1967 | Brechner et al. | 8/10.2 |
| 3,536,436 | 10/1970 | Lange | 8/10.2 |

*Primary Examiner*—Joseph E. Evans
*Assistant Examiner*—Vera C. Clarke
*Attorney, Agent, or Firm*—Hammond & Littell

[57] ABSTRACT

An aqueous hair dye preparation comprising an oxidation dyestuff combination of a coupling component and a developer component consisting of a tetraaminopyrimidine derivative or a water-soluble acid addition salt thereof, as well as a process for dyeing hair by utilizing this oxidation dyestuff combination.

9 Claims, No Drawings

OXIDATION HAIR DYES BASED UPON TETRAAMINOPYRIMIDINE DEVELOPERS

Matter enclosed in heavy brackets [ ] appears in the original patent but forms no part of this reissue specification; matter printed in italics indicates the additions made by reissue.

THE PRIOR ART

Of great importance for the dyeing of hair are the so-called oxidation dyestuffs because of their intensive colors and very good fastness. These dyestuffs are formed by the oxidative coupling of a developer component with a coupling component. The developers customarily used are nitrogenous bases, such as p-phenylenediamine derivatives, diaminopyridines, 4-aminopyrazolone derivatives or heterocyclic hydrazones. Useful as so-called coupling components are m-phenylenediamine derivatives, phenols, naphthols, resorcinol derivatives and pyrazolones.

Good oxidation dyestuff components for hair dyeing must fulfill all of the following requirements.

They have to be able to develop a sufficient intensity of the desired color shades when oxidatively coupled with the respective developer component or coupling component. Furthermore, they have to possess a capacity for being absorbed by human hair, which capacity ranges from sufficient to very good; and in addition, they should be unobjectionable from toxicological and dermatological viewpoints.

As developers, it is customary to use the class of compounds consisting of substituted or unsubstituted p-phenylenediamines. However, this class of compounds has the disadvantage that sensitivity reactions and subsequently severe allergies are caused in numerous persons. The developers which have been recently proposed for avoiding these dermatological disadvantages are not always fully satisfactory with respect to their technical application.

OBJECTS OF THE INVENTION

An object of the invention is to provide usable oxidation hair dyes containing suitable components which optimally satisfy the above requirements.

Another object of the present invention is to provide an oxidation dyestuff combination of a coupling component and a developer component, which is based on tetraaminopyrimidines as the developer component.

These and further objects of the present invention will become apparent as the description thereof proceeds.

DESCRIPTION OF THE INVENTION

The present invention provides a composition and process for dyeing hair based upon an oxidation dyestuff combination of a coupling component and a developer component with tetraaminopyrimidines being the developer component, as well as novel tetraaminopyrimidines. It has now been found that the abovespecified requirements can be fulfilled to an especially significant extent by the use of hair coloring preparations that are based on oxidation dyestuff combinations containing tetraaminopyrimidines of the formula

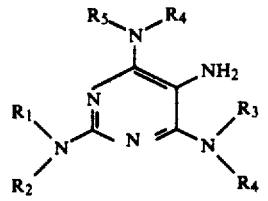

and their inorganic or organic water-soluble acid addition salts as developers, and containing the couplers customarily used in oxidation hair dyes, in which $R_1$ to $R_6$ are each selected from the group consisting of hydrogen, alkyl having 1 to 4 carbon atoms, aryl, substituted aryl and $—(CH_2)_n—X$, in which n is an integer from 1 to 4, and X is selected from the group consisting of hydroxy, halogen and $—NR_7R_8$ wherein $R_7$ and $R_8$ are selected from the group consisting of hydrogen and alkyl having 1 to 4 carbon atoms and can form with the nitrogen atom a heterocyclic ring which may contain one additional nitrogen atom or an oxygen atom. In the above formula, $R_1$ to $R_6$ likewise can designate an optionally substituted five-membered or six-membered heterocyclic ring containing one or two nitrogen atoms, or one nitrogen atom and one oxygen atom.

More particularly, the present invention is directed to an aqueous preparation for the dyeing of hair consisting essentially of (1) from 0.2% to 5% by weight of an oxidation dyestuff combination of a developer component, and a coupling component in substantially equimolar amounts, said developer component consisting essentially of (A) a tetraaminopyrimidine of the formula

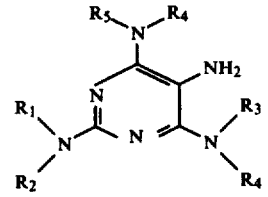

wherein $R_1$, $R_2$, $R_3$, $R_4$, $R_5$ and $R_6$ are each selected from the group consisting of hydrogen, phenyl, alkyl having 1 to 4 carbon atoms, phenylalkyl having 7 to 10 atoms, phenylalkenyl having 7 to 10 carbon atoms, $$X—(CH_2)_n—$$

wherein n is an integer from 1 to 4, and X is selected from the group consisting of hydroxyl, halogen and $NR_7R_8$— in which $R_7$ and $R_8$ are each hydrogen or alkyl having 1 to 4 carbon atoms, and together with the nitrogen atom $R_7$ and $R_8$ from a member selected from the group consisting of a 5 to 6 membered heterocyclic ring optionally containing an additional nitrogen atom or oxygen atom, and wherein $R_1$ and $R_2$, or $R_3$ and $R_4$, or $R_5$ and $R_6$, together with the nitrogen atom form a five to six membered heterocyclic ring optionally containing another nitrogen or oxygen atom in the ring and (B) a water-soluble acid addition salt of (A); (2) from 0% to 5% by weight of a direct dyestuff; (3) from 0% to 30% by weight of a surfactant; (4) from 0% to 25% by weight of thickeners; and (5) the balance up to 100% by weight of water.

A particularly preferred subgenus of the above-mentioned developer component is wherein $R_1$, $R_2$, $R_3$, $R_4$, $R_5$ and $R_6$ are each selected from the group consisting of hydrogen, methyl, ethyl, isopropyl, n-propyl, butyl, phenyl, benzyl and benzylidene, or $—(CH_2)_n—X$ wherein $R_1$ and $R_2$, or $R_3$ and $R_4$, or $R_5$ and $R_6$, together with the nitrogen atom form a substituent selected from the group consisting of hydroxyl, halogen and $—NR_7R_8$ in which $R_7$ and $R_8$ are each hydrogen or alkyl having 1 to 4 carbon atoms.

When the compounds according to the invention are used as developer components, they react with the known couplers generally used in oxidation hair dyestuffs to give very intensive, varying shades which previously heretofore could not be effected with these known couplers and these developers known so far. Thus, the compounds of the invention considerably increase the possibilities for utilizing oxidation hair dyes. Furthermore, the tetraaminopyrimidines according to the invention are distinguished by very good fastness of the dyeings effects with them, by good water-solubility, by good storage stability, and by excellent toxicological as well as dermatological unobjectionableness.

The tetraaminopyrimidines which are to be used as developer components according to the invention can be used either as such or in form of their water-soluble acid addition salts with non-toxic inorganic acids or organic acids, such as for example, hydrochloric acid, sulfuric acid, phosphoric acid, acetic acid, propionic acid, lactic acid or citric acid.

The preparation of most tetraaminopyrimidines to be used as developer components according to the invention is already known in the literature and can be taken from the monograph by D. J. Brown, in the series "Heterocyclic Compounds", Interscience Publishers, 1962, Vols. I and II, "The Pyrimidines". Only a few of the compounds used are novel substances, the preparation of which is separately described below.

Specific examples of the novel tetraaminopyrimidines according to the invention are 5-amino-2,4,6-tris(methylamino)-pyrimidine, 2,4,5-triamino-6-(di-n-propylamino)-pyrimidine and 2,4,5-triamino-6-morpholino-pyrimidine, or a water-solution acid addition salt thereof.

To synthesize the compounds to be used according to the invention, the starting material generally is a 2,4,6-aminopyrimidine, into which the 5-amino group is introduced by nitrosation and subsequent reduction. It is also possible to start from the correspondingly substituted triaminoalkylmercaptopyrimides and to replace the alkylmercapto group with an amino group. The latter method is especially suitable for the introduction of substituted amino groups into the 2-, 4-, or 6-positions of the pyrimidine ring. Suitable examples of developer components to be used according to the invention are, for example: 2,4,5,6-tetraamino-pyrimidine, 4,5-diamino-2,6-bis-(methylamino)-pyrimidine, 2,5-diamino-4,6-bis-(methylamino)-pyrimidine,
4,5-diamino-6-(butylamino)-2-(dimethylamino)-6-pyrimidine,
2,5-diamino-4-(diethylamino)-6-(methylamino)-pyrimidine,
4,5-diamino-6-(diethylamino)-(2-dimethylamino)-pyrimidine,
4,5-diamino-2-(diethylamino)-6-(methylamino)-pyrimidine,
4,5-diamino-2-(dimethylamino)-6-(ethylamino)-pyrimidine,
4,5-diamino-2-(dimethylamino)-6-(isopropylamino)-pyrimidine,
4,5-diamino-2-(dimethylamino)-6-(methylamino)-pyrimidine,
4,5-diamino-6-(dimethylamino)-2-(methylamino)-pyrimidine,
4,5-diamino-2-(dimethylamino)-6-(propylamino)-pyrimidine,
2,4,5-triamino-6-(dimethylamino)-pyrimidine,
4,5,6-triamino-2-(dimethylamino)-pyrimidine,
2,4,5-triamino-6-(methylamino)-pyrimidine,
4,5,6-triamino-2-(methylamino)-pyrimidine,
4,5-diamino-2-(dimethylamino)-6-piperidino-pyrimidine,
4,5-diamino-6-(methylamino)-2-piperidino-pyrimidine,
2,4,5-triamino-6-piperidino-pyrimidine,
2,4,5-triamino-6-anilino-pyrimidine,
2,4,5-triamino-6-(benzylamino)-pyrimidine,
2,4,5-triamino-6-(benzylideneamino)-pyrimidine,
4,5,6-triamino-2-piperidino-pyrimidine,
5-amino-2,4,6-tris-(methylamino)-pyrimidine,
2,4,5-triamino-6-(di-n-propylamino)-pyridine,
2,4,5-triamino-6-morpholino-pyrimidine,
2,[4]5,6-triamino-4-(dimethylamino)-pyrimidine
4,5,6-triamino-2-morpholino-pyrimidine,
2,4,5-triamino-6-(β-hydroxyethyl-amino)-pyrimidine,
4,5,6-triamino-2-[(β-aminoethyl)amino]-pyrimidine,
2,5,6-triamino-4-[(β-methylamino)-ethylamino]-pyrimidine,
2,5-diamino-4,6[bis-(γ-diethylamino)-propylamino]-pyrimidine,
4,5-diamino-6-[([B]β-hydroxyethyl)-amino]-2-(methylamino)-pyrimidine,
5-amino-2,4,6-(triethylamino)-pyrimidine, and
5-amino-6-anilino-2,4-[bis-(β-hydroxyethyl)-amino]-pyrimidine.

Generally speaking, the coupling components include 1-phenyl-pyrazol-5-ones, aromatic amines, aromatic alcohols, preferably m-aminophenols, 1,3-diamino-4-nitrobenzenes, 1,4-diamino-2-nitrobenzenes and pyrazolidine-diones.

Examples of coupling components include 1-phenyl-pyrazol-5-one derivatives of the formula

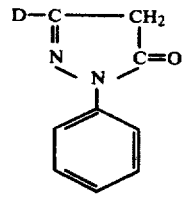

wherein D represents lower alkyl such as methyl, $NH_2$—,—NH—CO—$D_1$ or —NH—CO—NH—$D_1$ or NH—CS—NH—$D_1$ and $D_1$ denotes a hydrocarbon radical with 1 to 12 carbon atoms or a heterocylic radical, and preferably $D_1$ is alkyl having 1 to 6 carbon atoms such as methyl, ethyl, isopropyl, n-propyl, n-butyl; phenyl; halopenyl such as p-chlorophenyl; alkylphenyl having from 7 to 12 carbon atoms such as p-methylphenyl, p-ethylphenyl, o-propylphenyl; alkoxyphenyl, having from 7 to 12 carbon atoms such as o-methoxyphenyl p-isopropoxyphenyl; dialkylamino-phenyl having 1 to 4 carbon atoms in the alkyl such as p-dimethylaminophenyl; cyclohexyl; alkylcyclohexyl having from 7 to 12 carbon atoms such as methylcyclohexyl; pyridyl; and piperidyl.

Examples of readily available substituted 1-phenyl-3-aminopyrazol-5-ones are the following:

1-phenyl-3-amino-pyrazol-5-one,
1-phenyl-3-methyl-pyrazol-5-one,
1-phenyl-3-acetamido-pyrazol-5-one,
1-phenyl-3-benzamido-pyrazol-5-one,
1-phenyl-3-(3'-cyclohexylureido)-pyrazol-5-one,
1-phenyl-3-(3'-phenylureido)-pyrazol-5-one,
1-phenyl-3-(3'-p-chlorophenylureido)-pyrazol-5-one,
1-phenyl-3-(3'-ethyl-2'-thioureido)-pyrazol-5-one,
1-phenyl-3-(3'-n-butyl-2'-thioureido)-pyrazol-5-one,
1-phenyl-3-(3'-phenyl-2'-thioureido)-pyrazol-5-one,
1-phenyl-3-(3'methylureido)-pyrazol-5-one,
1-phenyl-3-(3'-ethylureido)-pyrazol-5-one,
1-phenyl-3-(3'-n-propylureido-pyrazole-5-one,
1-phenyl-3-(3'-isopropylureido)-pyrazol-5-one, and
1-phenyl-3-(3'-n-butylureido)-pyrazol-5-one.

Another coupling component for the hair dyes is based on aromatic amines and/or aromatic alcohols, preferably a compound having the formula E—Ar—F in which Ar represents an aromatic nucleus, preferably consisting of naphthylene, hydroxynaphthylene, aminonaphthylene, phenylene, aminophenylene, hydroxyphenylene, toluylene, alkoxyphenylene having from 7 to 10 carbon atoms and quinolylene; E represents hydrogen, hydroxyl, or amino, dialkylamino having from 1 to 4 carbon atoms in the alkyls; and F represents hydroxyl, amino or dialkylamino having from 1 to 4 carbon atoms in the alkyls.

Suitable coupling components include aromatic amines and diamines, phenols, naphthols and aminophenols. The metacompounds are preferably used in the case of the diamines, aminophenols and phenols. When diamines are used, those in which the hydrogen atoms of the amino groups are substituted by lower alkyl residues ($C_1$–$C_4$) may also be used.

The following compounds are examples of the said coupling components:

m-cresol,
m-phenylenediamine,
o-cresol,
m-aminophenol,
anisidine,
2,4-diaminoanisole,
m-toluylenediamine,
resorcinol,
pyrogallol,
pyrocathechol,
resorcinol-monoethyl ether
resorcinol-monomethyl ether,
m-aminoresorcinol,
1,5-dihydroxynaphthalene,
1,6-dihydroxynaphthalene,
1,7-dihydroxynaphthalene,
2,7-dihydroxynaphthalene,
1,5-amino- or 1,8-amino-hydroxynaphthalene,
α-naphthol,
7-(dimethylamino)-4-hydroxy-1-methyl-2-quinoline,
8-hydroxyquinoline,
1,8-diaminonaphthalene,
2,6-dimethyl-phenol,
2,5-dimethyl-phenol,
3,4-dimethyl-phenol,
3,5-dimethyl-phenol,
5-amino-2-methyl-phenol,
hydroquinone,
4-aminophenol, Other coupling compounds include 1,3-diamino-4-nitrobenzene derivatives of the formula

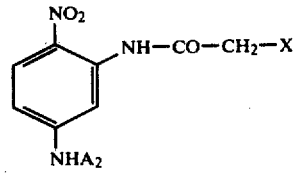

and 1,4-diamino-2-nitrobenzene derivatives of the formula

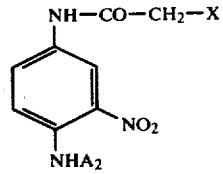

in which X is an electrophilic substituent and $A_2$ is a member selected from the group consisting of hydrogen, alkyl of 1 to 10 carbon atoms, hydroxyalkyl of 1 to 10 carbon atoms; N,N-dialkyl-aminoalkyl of 3 to 18 carbon atoms, alkanoyl of 2 to 10 carbon atoms, substituted alkanoyl of 2 to 10 carbon atoms with a substituent selected from the group consisting of nitro, phenyl, halo, cyano, carboxy and sulfo, acyl of aromatic hydrocarbon carboxylic acids having 7 to 15 carbon atoms, substituted acyl of aromatic hydrocarbon carboxylic acids having from 7 to 15 carbon atoms with a substituent selected from the group consisting of lower alkyl, nitro, halo, cyano, carboxyl and sulfo, and the activated methylene group —CO—$CH_2$—X, in which X is an electrophilic substituent.

An electrophilic substituents X, the radicals containing a carbonyl, such as carboxyl, alkoxycarbonyl, and acyl, or a nitrile, or carbonyl containing radicals further substituted with halogen, the sulfo group and the nitro group, are considered. X is preferably a nitrile, acyl, or alkoxycarbonyl group.

Examples of X include carboxyl, cyano, alkanoyl of 2 to 10 carbon atoms, substituted alkanoyl of 2 to 10 carbon atoms with a substituent selected from the group consisting of nitro, phenyl, halo, cyano, carboxyl and sulfo, acyl of aromatic hydrocarbon carboxylic acids having 7 to 15 carbon atoms, substituted acyl of aromatic hydrocarbon carboxylic acids having from 7 to 15 carbon atoms with a substituent selected from the group consisting of lower alkyl, nitro, halo, cyano, carboxyl and sulfo, cycloalkylcarbonyl of 6 to 10 carbon atoms, alkoxylcarbonyl of 2 to 10 carbon atoms, cycloalkoxycarbonyl of 6 to 10 carbon atoms, phenylalkoxycarbonyl of 8 to 16 carbon atoms, furoyl, and thenoyl.

Suitable examples for compounds of the above described diamino-nitrobenzenes are as follows:

1-amino-3-cyanoacetylamino-4-nitrobenzene,
1-benzoylacetylamino-3-amino-4-nitrobenzene,
1-methylamino-3-cyanoacetylamino-4-nitrobenzene, 1,3-di(cyanoacetylamino)-4-nitrobenzene,
1,3-Di(ω-ethoxycarbonyl-acetylamino)-4-nitrobenzene,
1-Amino-3(ω-ethoxycarbonyl-acetylamino)-4-nitrobenzene,
1-Acetylamino-3-cyanoacetylamino-4-nitrobenzene,
1-Amino-3-acetoacetylamino-4-nitrobenzene,
1-(ρ-Nitro-benzylacetylamino)-3-amino-4-nitrobenzene,
1-Trifluoro-acetoacetylamino-3-amino-4-nitrobenzene,
1-(2-Hydroxy-ethylamino)-3-cyanoacetylamino-4-nitrobenzene,
1-Amino-2-nitro-4-ω-cyanoacetylamino-benzene,
1-Amino-2-nitro-4-ω-benzoyl-acetylamino-benzene,
1,4-Dicyanoacetylamino-2-nitrobenzene,
1-Amino-2-nitro-4-ω-ethoxycarbonyl-acetylamino-benzene,
1,4-Bis-(ω-ethoxycarbonyl-acetylamino)-2-nitrobenzene,
1-Amino-2-nitro-4ω-benzoxycarbonyl-acetylamino-benzene,
1-Amino-2-nitro-4-(ρ-nitrobenzoyl-acetylamino)-benzene,
1-Amino-2-nitro-4-acetoacetylamino-benzene,
1-Amino-2-nitro-4-nitroacetoacetylamino-benzene,
1-Amino-2-nitro-4-trifluoroacetoacetylamino-benzene,
1-Amino-2-nitro-4-ω-butyryl-acetylamino-benzene,
1-Amino-2-nitro-4-ω-(β-Naphthoylacetylamino)-benzene,
1-Amino-2-nitro-4-cyclohexylcarbonyl-acetylamino-benzene,
1-Amino-2-nitro-4-Furoylacetylamino-benzene,
1-Amino-2-nitro-4-Thenoylacetylamino-benzene,
1,4-Bis-(ω-butoxycarbonyl-acetylamino)-benzene,
1,4-Bis-(ω-cyclohexyloxycarbonyl-acetylamino)-benzene.

Further coupling components include pyrazolidinediones such as 1-phenyl-3,5-pyrazolidine dione.

Specific examples of preferred coupling components to be used for the hair dyes according to the invention are as follows:

α-naphthol,
o-cresol,
m-cresol,
2,6-dimethylphenol,
2,5-dimethylphenol
3,4-dimethylphenol,
3,5-dimethylphenol
pyrocatechol,
pyrogallol
1,5-dihydroxy-naphthalene,
1,7-dihydroxy-naphthalene,
5-amino-2-methylphenol,
hydroquinone,
2,4-diaminoanisole,
m-toluylenediamine
4-aminophenol,
resorcinol,
resorcinol monomethyl ether m-phenylenediamine,
3-methyl-1-phenyl-pyrazolone-5,
3-amino-1-phenyl-pyrazolone-5,
1-phenyl-3,5-dione-pyrazolidine,
7-(dimethylamino)-4-hydroxy-1-methyl-quinolone-2,
1-amino-3-(acetacetylamino)-4-nitrobenzene,
1-amino-3-(cyanoacetylamino)-4-nitrobenzene.

In order to obtain shades which are as strong as possible and which correspond to natural hair colors to a large extent, it is very important to use a superior blue dye as shade component. In the preparation of natural looking shades with the aid of coupler components for producing blue dyes, there are, however, difficulties encountered with the customary blue-couplers even when the otherwise very satisfactory tetraaminopyrimidines are used as developers.

It has now been found that this drawback can be corrected when, in combination with the tetraaminopyrimidines employed as developers, the following m-aminophenols are used as the coupling components. These m-aminophenols have the formula

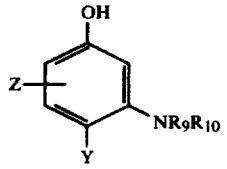

wherein Z and Y are each selected from the group consisting of hydrogen, halogen, hydroxyl, amino, alkyl having 1 to 4 carbon atoms, alkoxy having 1 to 4 carbon atoms, alkylamino having 1 to 4 carbon atoms, dialkylamino having 1 to 4 carbon atoms in each of the alkyls; $R_9$ is selected from the group consisting of alkyl having 1 to 10 carbon atoms, phenyl optionally substituted, benzyl, methylenecyanamido, propionamido, ureido, thioureido, oxalyl ester having 1 to 4 carbon atoms in the alcohol moiety, $M—(CH_2)_m—$in which m is an integer from 1 to 4 and M is selected from the group consisting of hydroxyl, halogen, and$—NR_{11}R_{12}$ in which $R_{11}$ and $R_{12}$ are each hydrogen or alkyl having 1 to 4 carbon atoms, and in which $R_9$ and $R_{10}$ can together with the nitrogen atom form an optionally substituted five- or six-membered heterocyclic ring which may contain an additional nitrogen atom or an oxygen atom, and $R_{10}$ is selected from the group consisting of hydrogen and $R_9$.

More particularly the coupling component is selected from the group consisting of (a) m-aminophenol of the formula

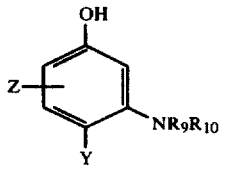

wherein Z and Y are each selected from the group consisting of hydrogen, halogen, hydroxyl, amino, alkyl having 1 to 4 carbon atoms, alkoxy having 1 to 4 carbon atoms, alkylamino having 1 to 4 carbon atoms, dialkylamino having 1 to 4 carbon atoms in each of the alkyls;

Wherein $R_9$ is selected from the group consisting of alkyl having 1 to 10 carbon atoms, hydroxyalkyl having 1 to 10 carbon atoms, phenyl, anilino, hydroxyphenyl, benzyl, methylenecyanamido, propionamido, ureido, thioureido, oxalyl ester of an alcohol having 1 to 4 carbon atoms, $M—(CH_2)_m—$ wherein m is an integer from 1 to 4 and M is selected from the group consisting of hydroxyl, halogen, and $-NR_{11}R_{12}$, in which $R_{11}$ and $R_{12}$ are each hydrogen or alkyl having 1 to 4 carbon atoms and wherein $R_{10}$ is selected from the group consisting of hydrogen and $R_9$, wherein $R_9$ and $R_{10}$ can together with the nitrogen atom form a member selected from the group consisting of a five- or six-membered heterocyclic ring optionally containing in the ring oxygen or nitrogen and b. a water-soluble acid addition salt of (a).

A particularly preferred subgenus of said coupling component is wherein Z and Y are each selected from the group consisting of hydrogen, methyl, methoxy, amino, chloro, and hydroxyl;

wherein $R_9$ is selected from the group consisting of methyl, ethyl, octyl, propyl, hydroxyethyl, phenyl, benzyl, anilino, hydroxyphenyl, ureido, thioureido, methylene-cyanamido, and diethylaminoethyl, wherein $R_{10}$ is selected from the group consisting of hydrogen and $R_9$, and wherein $R_9$ and $R_{10}$ together with the nitrogen atom form a member selected from the group consisting of pyrrolidino, morpholino, and piperidino.

The m-aminophenol derivatives to be employed as blue-coupling component can be used either as such or in form of their water-soluble acid addition salts with inorganic or organic acids, such as for example, hydrochloric acid, sulfuric acid, phosphoric acid, acetic acid, propionic acid, lactic acid and citric acid.

Suitable examples of blue-coupling components to be employed according to the invention are as follows:

3-(dimethylamino)-phenol,
3-(diethylamino)-phenol,
3-(dioctylamino)-phenol,
3-(ethylmethylamino)-phenol,
3-(ethylpropylamino)-phenol,
3-(phenylethylamino)-phenol,
3-(phenyloctylamino)-phenol,
3-(benzylamino)-phenol,
3-(ethylbenzylamino)-phenol,
3-anilinophenol,
3-(methylamino)-phenol,
3-(ethylamino)-phenol,
3-(octylamino)-phenol,
3-(ethylureidoamino)-phenol,
3-ureidophenol,
3-(phenylureidoamino)-phenol,
3-(β-hydroxyethyl amino)-phenol,
3-(N-β-hydroxyethyl-N-methyl-amino)-phenol,
3-(thioureidoamino)-phenol,
N-ethyl-N-(3-hydroxyphenyl)-urea,
3-(methylenecyanamido)-phenol,
3-((2-diethylamino)-ethyl)-amino)-phenol,
3-N-(2-diethylaminoethyl)-N-methyl-aminophenol,
3-pyrrolidinophenol,
3-morpholinophenol,
3-piperidinophenol,
5-(ethylamino)-2-methylphenol,
5-(diethylamino)-2-methylphenol
3-ethylamino)-4-methoxyphenol,
3-diethylamino)-4-methoxyphenol,
2-chloro-5-(dimethylamino)-phenol
3,5-dihydroxy-N,N-dimethylaniline,
2-amino-5-(diethylamino)-phenol,
6-chloro-3-(diethylamino)-5-hydroxy-toluene,
3-anilino-6-chloro-5-hydroxy-toluene,
5-methyl-3-piperidino-phenol, and
4-chloro-3-pyrrolidino-phenol.

The preparation of the m-aminophenol derivatives to be used as blue-coupling components is already known from the literature. See the article of F. Effenberger et al in Chem. Ber. 103, 1456–62, (1970) and British Pat. No. 974,343. The preparation of several novel derivatives which were not found in the literature is separately described below.

Specific examples of novel m-aminophenols are as follows: 3-(diethylamino)-4-methoxy-phenol, 5-(ethylamino)-2-methyl-phenol and 5-(diethylamino)-2-methyl-phenol, as well as water-soluble acid addition salts thereof.

In the hair coloring preparations according to the invention, substantially equimolar quantities of the developer components are used based on the coupling components employed. Although an equimolar amount is preferred, it is possible to use more or less than molar amounts. Furthermore, the developer component and the coupling component may be used as pure ingredients or as mixtures. Not only can the developer component consist of mixtures of the tetraaminopyrimidines to be used according to the invention, but the coupling component can also consist of mixtures of the above-named coupling components.

In addition, the hair coloring preparations according to the invention can contain admixtures of other customary developing components and, if necessary, can also contain the customary direct dyestuffs in case the latter are needed for obtaining certain shades. From 0% to 5% direct dyestuffs may be employed. As in the case of other oxidation hair dyes, the oxidative coupling, i.e., the development of the dye can in principle be effected by atmospheric oxygen. Moreover, it is preferred to use chemical oxidizing agents. Suitable examples are especially hydrogen peroxide or its products of addition to urea, melamine and sodium borate, as well as mixtures of such hydrogen peroxide addition products with potassium peroxydisulfate.

When the tetraaminopyrimidines according to the invention are used as developer components, they have the advantage that the oxidative coupling with atmospheric oxygen readily produces highly satisfactory hair dyeing results. Thus, damage to the hair by the oxidizing agents, otherwise employed for oxidative coupling, can be prevented.

In the situation that a bleaching of the hair is simultaneously desired, then the concurrent use of chemical oxidizing agents is necessary.

For application, the hair dyes according to the invention are incorporated into suitable aqueous cosmetic preparations, such as creams, emulsions, gels or simple solutions and immediately before application to the hair, one of the above-named oxidizing agents is added. These hair dyeing preparations contain coupling and developing components in amounts of from 0.2% to 5% by weight, preferably from 1% to 3% by weight.

For the preparation of creams, emulsions or gels, the dye components are mixed with the additional ingredients customarily used in such preparations. Such additional ingredients are, for example, wetting agents or emulsifiers of the anionic or nonionic type, such as alkylbenzenesulfonates, higher fatty alcohol sulfates, higher alkylsulfonates, higher fatty acid alkanolamides, ethoxylated fatty alcohols; thickeners such as methyl cellulose, starch, higher fatty alcohols, paraffin oil and higher fatty acids. Furthermore, perfumes and hair-conditioning and grooming agents, such as panthothenic acid and cholesterol may be included.

Effective amounts of the above-named additives are those customarily employed for this purpose. Effective amounts of wetting agents range from 0.5% to 30% by weight, preferably from 1% to 15% by weight; and for thickeners, an effective amount ranges from 0.1% to 25% by weight, preferably from 1% to 15% by weight, based in each case on the total weight of the preparation. As a lower limit for the above additives, a zero percent lower limit is possible, if none of the additive is utilized.

The hair coloring preparations according to the invention can be applied in a weakly acid medium, a neutral medium or especially, in an alkaline medium, preferably at a pH of 8 to 10, regardless whether a solution, an emulsion, a cream, or a gel is employed.

These preparations are applied at a temperature which usually ranges from 15° C. to 40° C. and preferably is room temperature.

After the preparation has been allowed to react for about 30 minutes, the hair coloring preparation is removed from the hair to be dyed, by rinsing. Then the hair is washed with a mild shampoo, and finally is dried.

When different developer and coupling components are used, the shades obtainable by use of the hair coloring preparations according to the invention have the advantage of providing an extraordinary variations which extend from ash blond to dark brown and green to violet. The properties of the hair colors produced are excellent as far as fastness to light and washing are concerned, as well as good resistance to abrasion is concerned; and the hair dyes once fixed can be easily removed by means of reducing agents.

The following examples are merely illustrative of the present invention without being deemed limitative in any manner thereof.

EXAMPLES

First, there are examples for the preparation of some novel tetraminopyrimidines which are utilized according to the invention, but have not been previously described in the literature.

EXAMPLE 1

Preparation of

5-Amino-2,4,6-tris-(methylamino)-pyrimidine Sulfate, $C_7H_{14}N_6 \cdot H_2SO_4 \cdot 2H_2O$ 2,4,6-tris(methylamino)-pyrimidine was prepared according to Winkelmann, J. Pract. Chem. 115, 292 (1927) and 5.5 gm of this compound were dissolved in 50 ml water. The solution was adjusted to a pH of 4 by means of sodium acetate and was then heated to 80° C.; and a solution of 1.4 gm of $NaNO_2$ in 5 ml of $H_2O$ was added to form a red solution. At 60° C., sodium dithionite was added until the solution became yellow. Dilute $H_2SO_4$ was added to the yellow solution; and the precipitate was vacuum filtered. The yield was 55%; and the melting point was 215° C.

| Elemental Analysis: | % C | % H | % N |
|---|---|---|---|
| Found: | 26.6 | 6.4 | 26.6 |
| Calculated: | 26.6 | 8.3 | 27.7 |

EXAMPLE 2

Preparation of 2,4,5-Triamino-6-(di-n-propylamino)-pyrimidine

Dihydrochloride, $C_{10}H_{20}H_6 \cdot 2\ HCl$ 2,4,5-Triamino-6-(di-n-propylamino)pyrimidine dihydrochloride was prepared stepwise as follows:

1. 2,4-Diamino-6-(di-n-propylamino)-pyrimidine 2,4-Diamino-6-chloropyrimidine was prepared according to Roth et al, J. Amer. Chem. Soc. 72, 1914 (1950). To 15 gm of this compound in 130 ml of ethanol, there was added 50 gm of di-n-propylamine, and the mixture was heated in an autoclave at 200° C. for three hours (at an initial gauge pressure of 10 atm. of $N_2$). After the autoclave had cooled and had been opened, the reaction mixture was cooled in an ice-salt bath to precipitate dipropylamine hydrochloride. After filtration, the mother liquor was considerably concentrated to give a residue of about 30 ml, whereby 18 gm or 82.9% of theory of crude raw product precipitated. This product was used as such for subsequent synthesis.

2. 2,4-Diamino-6-(di-n-propylamino)-5nitrosopyrimidine 18 gm of the crude product 2,4-diamino-6-(di-n-propylamino)-pyrimidine was suspended in 25 ml of water; and glacial acetic acid was added until a pH of 4 was reached. After heating to 50° C. had resulted in solution of the substance, 5.5 gm of sodium nitrite in 10 ml of water were slowly added. After a short time, a raspberry red precipitate was deposited, vacuum filtered, and dried under vacuum at room temperature. The remainder weighed 9.4 gm which was 46% theory; and had a melting point of 206°-208° C.

| Elemental Analysis: | % C | % H | % N |
|---|---|---|---|
| Found: | 50.40 | 7.61 | 35.27 |
| Calculated: | 49.56 | 7.62 | 35.50 |

3. 2,4,5-Triamino-6-(di-n-propylamino)-pyrimidine Dihydrochloride 6.5 gm of 2,4-diamino-6-(di-n-propylamino)-5-nitrosopyrimidine in 150 ml of ethanol with 0.5 gm of catalyst (10% palladium-on-charcoal) were introduced into a pressure-tested hydrogenation vessel to be hydrogenated at room temperature in a catalytic apparatus of the shaker type. After $H_2$-absorption had terminated, the catalyst was removed by filtration; the solution was acidified with hydrochloric acid, and concentrated. The residue was 5.6 gm which was 78.8% of theory of brown crystals; melting point (decomp.) was 105° C. The mass spectrum showed the molecular mass to be 224 (calcd.: 224).

EXAMPLE 3

Preparation of 2,4,5-Triamino-6-morpholino-pyrimidine Sulfate, $C_8H_{14}N_6O \cdot H_2SO_4$ 2,4,5-Triamino-6-morpholino-pyrimidine sulfate was prepared stepwise from the following compounds:

1. 2,4-Diamino-6-morpholinopyrimidine 2,4-diamino-6-chloropyrimidine was prepared according to Roth et al, J. Amer. Chem. Soc. 72, 1914 (1950). To 10 gm of this compound, (0.07 mol), 30 gm of morpholine (30 ml, 0.34 mol) were added; and while stirring, the mixture was heated to 100° C. within one hour. The mixture was kept at this temperature for 2½ hours. Then, 10 ml of ethanol were added; and the mixture was stored in a refrigerator until morpholine hydrochloride had precipitated. After removal of this salt, the filtrate was concentrated to produce the crude product which was half oily, half crystalline residue. There was 5.9 gm which constituted 43.7% of theory; and this crude product was utilized for subsequent synthesis.

2. 2,4-Diamino-6-morpholine-5-nitroso-pyrimidine 5.9 gm of the crude 2,4-diamino-6-morpholino-pyrimidine (0.03 mol), were dissolved by heating in 25 ml of water; and glacial acetic acid was added until a pH of 4 was reached. Then the solution was heated to 80° C., and a solution of 2 gm of sodium nitrite in 5 ml of water was slowly added. After a short time, the nitroso compound was obtained as a raspberry red precipitate. Concentration and cooling produced a total yield of a 4.1 gm which was 60.3% of theory. The melting point was 231°-233° C.

| Elemental Analysis: | % C | % H | % N |
|---|---|---|---|
| Found: | 42.85 | 5.39 | 37.48 |
| Calculated: | 41.92 | 4.97 | 38.22 |

3. 2,4,5-Triamino-6-morpholino-pyrimidine Sulfate 2.5 gm of 2,4-diamino-6-morpholino-5-nitroso-pyrimidine was suspended in 15 ml of water, and 2 N HCl (5 ml) was added until the substance just dissolved. The mixture was heated to 50° C.; and sodium dithionite ($Na_2S_2O_4$) was added until the violet color solution took on a yellow color. Then, the solution was filtered, cooled, and adjusted to a pH 2 by means of sulfuric acid (1:1). After a short time, the pyrimidine derivative precipitated as pyrimidine sulfate; the yield was 2.6 gm which was 76.4% of theory.

| Elemental Analysis (of the recrystallized compound): | % C | % H | % N |
|---|---|---|---|
| Found: | 31.17 | 5.23 | 27.2 |
| Calculated: | 29.81 | 4.98 | 27.8 |

Melting Point: the compound sintered at 230° slow decomposition from 255° C. on.

Melting Point: the compound sintered at 230° slow decomposition from 255° C. on.

The other tetraaminopyrimidines which were used in the following Examples were reported in the literature and were prepared by the synthesis indicated in the monograph of D. J. Brown, "The Pyrimidines" in the series of Heterocyclic Compounds, Interscience Publishers, 1962, Vols. I and II.

Several m-aminophenol derivatives which were used as blue-coupling components in the hair coloring preparations according to the invention are novel and are not found in the literature. Hence, their preparation is described in the following examples.

EXAMPLE 4

3-(Diethylamino)-4-methoxyphenol Hydrochloride 8.3 gm ethyl bromide were added to a solution of 10.5 gm of 3-amino-4-methoxyphenol in 50 ml of ethanol. The reaction mixture was refluxed for 24 hours. After the solution had cooled, it was diluted with 800 ml of water; and the pH was adjusted to slight alkalinity by the addition of sodium carbonate. The solution was repeatedly extracted with ether, and the combined extracts were dried over anhydrous sodium sulfate. After the precipitate had been filtered off, the residue was concentrated; and the remaining residue as dissolved in 50 ml of ethanol. Then, after 8.7 gm of ethyl bromide had been added, the alkylation and treatment of the product were repeated as described above with the exception that this time, the dried ether extract was only concentrated to a volume of about 300 ml and dry HCl gas was passed into the solution while it was being cooled with ice. The precipitate was vacuum filtered; the residue was dried, dissolved in ethanol, and treated with active charcoal. Addition of ether to the ethanolic solution resulted in the precipitation of the pure product, which had a melting point of 197°-198° C.

| Elemental Analysis: | % C | % H | % N | Cl |
|---|---|---|---|---|
| Found: | 57.1 | 7.8 | 6.03 | 15.3 |
| Calculated: | 56.3 | 7.8 | 5.4 | 14.6 |

Mass Spectrum: 195 (calcd.: 195).

EXAMPLE 5

5-(Ethylamino)-2-methylphenol 88.6 gm of ethyl bromide were added to a solution of 50 gm of 5-amino-2-methylphenol in 250 ml of ethanol; and the mixture was refluxed for four hours. After the solution had cooled, it was diluted with 1.2 liters of water and was made weakly alkaline with sodium carbonate. After repeated extraction with ether, the ether extracts were dried and concentrated. The residue was recrystallized from ethanol, and had a melting point of 128° C. to 129° C.

| Elemental Analysis: | % C | % H | % N |
|---|---|---|---|
| Found: | 71.5 | 8.6 | 9.3 |
| Calculated: | 70.79 | 8.51 | 9.5 |

Mass Spectrum: 151 (calcd.: 151)

EXAMPLE 6

5-(Diethylamino)-2-methylphenol Hydrochloride 5 gm of 5-(ethylamino)-2-methylphenol were dissolved in 50 ml of ethanol, then alkylated analogously to the procedure described in Example 4 with 5,2 gm ethyl bromide, and worked up. The hydrochloride had a melting point of 192° C.

| Elemental Analysis: | % C | % H | % N | % Cl |
|---|---|---|---|---|
| Found: | 61.3 | 8.4 | 6.5 | 16.5 |
| Calculated: | 62.9 | 8.8 | 6.8 | 15.9 |

Mass Spectrum: 179 (calcd.: 179)

The hair dyes according to the invention were applied in form of an aqueous preparation such as an emulsified cream. The emulsion contained 10 parts by weight of fatty alcohols having 12 to 18 carbon atoms, 10 parts by weight of fatty alcohol sulfate (sodium salt) having 12 to 18 carbon atoms and 75 parts by weight of water.

Into each emulsion, there was incorporated 0.01 mol of the tetraaminopyrimidines and couplers which are listed in the following Table I. Then, the pH-value of the emulsion was adjusted to 9.5 with ammonia, and the emulsion was made up to 100 parts by weight with water. The oxidative coupling was effected by using as an oxidizing agent either atmospheric oxygen, or a 1% hydrogen peroxide solution with the proviso that 10 parts by weight of hydrogen peroxide solution were added to 100 parts by weight of the emulsion. The respective dyeing cream, with or without additional oxidizing agent, was applied to human hair that was 90% gray and that had not been pretreated in a special manner. After the cream had remained on the hair for 30 minutes to complete the dyeing process, the hair was washed with a customary shampoo and then dried. The shades thereby obtained are also listed in the following Table I.

TABLE 1

| | | | Shade obtained | |
|---|---|---|---|---|
| Example | Developer | Coupler | With Atmospheric $O_2$ | with 1% $H_2O_2$ |
| 7 | 2,4,5,6-Tetra-amino-pyrimidine | m-Phenylenediamine | olive | olive |
| 8 | 2,4,5,6-Tetra-amino-pyrimidine | 2,4-Diaminoanisole | dark green | dark green |
| 9 | 2,4,5,6-Tetra-amino-pyrimidine | m-diamino toluene | yellowish brown | yellowish brown |
| 10 | 2,4,5,6-Tetra-amino-pyrimidine | m-aminophenol | violet brown | violet brown |
| 11 | 2,4,5,6-Tetra-amino-pyrimidine | Resorcinol | strawberry red | grayish red |
| 12 | 2,4,5,6-Tetra-amino-pyrimidine | 3-Amino-1-phenyl-pyrazolone-5 | brownish orange | brownish orange |
| 13 | 2,4,5,6-Tetra-amino-pyrimidine | 3-Methyl-1-phenyl-pyrazolone-5 | brownish red | brownish orange |
| 14 | 2,4,5,6-Tetra-amino-pyrimidine | Resorcinol monomethyl ether | golden brown | golden brown |
| 15 | 2,4,5,6-Tetra-amino-pyrimidine | Naphthol | yellowish brown | yellowish brown |
| 16 | 2,4,5,6-Tetra-amino-pyrimidine | 1,5-Dihydroxy-Naphthalene | havanna brown | havanna brown |
| 17 | 2,4,5,6-Tetra-amino-pyrimidine | 1,7-Dihydroxy-Naphthalene | olive brown | olive brown |
| 18 | 4-Dimethylamino-2,5,6-Triamino-pyrimidine | m-Phenylenediamine | yellowish brown | yellowish brown |
| 19 | 4-Dimethylamino-2,5,6-Triamino-pyrimidine | 2,4-Diaminoanisole | olive yellow | olive yellow |
| 20 | 4-Dimethylamino-2,5,6-Triamino-pyrimidine | m-Diaminotoluene | yellowish brown | yellowish brown |
| 21 | 4-Dimethylamino-2,5,6-Triamino-pyrimidine | m-Aminophenol | burgundy red | burgundy red |
| 22 | 4-Dimethylamino-2,5,6-Triamino-pyrimidine | Resorcinol | brownish red | brownish red |
| 23 | 4-Dimethylamino-2,5,6-Triamino-pyrimidine | 3-Amino-1-Phenyl-pyrazolone-5 | raspberry red | raspberry red |
| 24 | 4-Dimethylamino-2,5,6-Triamino-pyrimidine | m-Phenylenediamine | olive brown | olive brown |
| 25 | 2-Dimethylamino-4,5,6-triamino-pyrimidine | m-Phenylenediamine | dark green | dark green |
| 26 | 2-Dimethylamino-4,5,6-triamino-pyrimidine | 2,4-Diaminoanisole | dark green | dark green |
| 27 | 2-Dimethylamino-4,5,6-triamino-pyrimidine | m-Diaminotoluene | olive-tinged yellow | olive-tinged yellow |
| 28 | 2-Dimethylamino-4,5,6-triamino-pyrimidine | m-Aminophenol | grayish violet | dark violet |
| 29 | 2-Dimethylamino-4,5,6-triamino-pyrimidine | Resorcinol | reddish violet | reddish violet |
| 30 | 2-Dimethylamino-4,5,6-triamino-pyrimidine | 3-Amino-1-phenyl-pyrazolone-5 | brick red | brick red |
| 31 | 2-Dimethylamino-4,5,6-triamino-pyrimidine | 3-Methyl-1-phenyl-pyrazolone-5 | lake red | grayish orange |
| 32 | 2-Dimethylamino- | Naphthol | hair | olive |

TABLE 1-continued

| Example | Developer | Coupler | Shade obtained With Atmospheric $O_2$ | Shade obtained with 1% $H_2O_2$ |
|---|---|---|---|---|
| | 4,5,6-triamino-pyrimidine | | brown | brown |
| 33 | 2-Dimethylamino-4,5,6-triaminio-pyrimidine | 3-acetoacetylamino-1-amino-4-nitrobenzene | yellowish brown | brass yellow |
| 34 | 2-Dimethylamino-4,5,6-triamino-pyrimidine | 1-Phenyl-3,5-pyrazolidine-dione | brownish orange | gray red |
| 35 | 2-Dimethylamino-4,5,6-triamino-pyrimidine | o-Cresol | brownish orange | ivory |
| 36 | 2-Dimethylamino-4,5,6-triamino-pyrimidine | m-Cresol | brownish orange | ivory |
| 37 | 2-Dimethylamino-4,5,6-triamino-pyrimidine | 2,5-Dimethylphenol | brownish red | grayish green |
| 38 | 2-Dimethylamino-4,5,6-triamino-pyrimidine | 3,4-Dimethylphenol | brownish orange | grayish green |
| 39 | 2-Dimethylamino-4,5,6-triamino-pyrimidine | 3,5-Dimethylphenol | brownish orange | grayish orange |
| 40 | 2-Dimethylamino-4,5,6-triamino-pyrimidine | 1,5-Dihydroxy-Naphthalene | brown | brown |
| 41 | 2-Dimethylamino-4,5,6-triamino-pyrimidine | Pyrogallol | chocolate brown | zinc gray |
| 42 | 2-Dimethylamino-4,5,6-triamino-pyrimidine | Pyrocatechol | reddish brown | fallow |
| 43 | 2-Dimethylamino-4,5,6-triamino-pyrimidine | 7-(Dimethylamino)-4-hydroxy-1-methyl-2-quinolone | grayish orange | golden blond |
| 44 | 2-Dimethylamino-4,5,6-triamino-pyrimidine | 5-Amino-2-methyl-phenol | brown | brown |
| 45 | 2-Dimethylamino-4,5,6-triamino-pyrimidine | Hydroquinone | brownish red | golden blond |
| 46 | 2-Piperidino-4,5,6-triamino-pyrimidine | m-Phenylenediamine | dark green | dark green |
| 47 | 2-Piperidino-4,5,6-triamino-pyrimidine | m-Aminophenol | dark violet | dark violet |
| 48 | 2-Piperidino-4,5,6-triamino-pyrimidine | Resorcinol | grayish ruby | grayish ruby |
| 49 | 2-Piperidino-4,5,6-triamino-pyrimidine | 2,4-Diaminoanisole | dark green | dark green |
| 50 | 2-Piperidino-4,5,6-triamino-pyrimidine | m-Diaminotoluene | brownish orange | brownish orange |
| 51 | 2-Piperidino-4,5,6-triamino-pyrimidine | 3-Amino-1-phenyl-pyrazolone-5- | tomato red | tomato red |
| 52 | 2-Morpholino-4,5,6-triamino pyrimidine | m-Phenylenediamine | olive | olive |
| 53 | 2-Morpholino-4,5,6-triamino-pyrimidine | m-Aminophenol | dark violet | dark violet |
| 54 | 2-Morpholino-4,5,6-triamino-pyrimidine | Resorcinol | grayish ruby | grayish ruby |
| 55 | 2-Morpholino-4,5,6-triamino-pyrimidine | 2,4-Diaminoanisole | dark green | dark green |
| 56 | 2-Morpholino-4,5,6-triamino-pyrimidine | m-Diaminotoluene | olive brown | olive brown |
| 57 | 2-Morpholino-4,5,6-triamino-pyrimidine | 3-Amino-1-phenyl-pyrazolone-(5) | brownish red | brownish red |
| 58 | 2-Methylamino- | m-Phenylenediamine | olive | olive |

TABLE 1-continued

| Example | Developer | Coupler | Shade obtained With Atmospheric $O_2$ | Shade obtained with 1% $H_2O_2$ |
|---|---|---|---|---|
| | 4,5,6-triamino-pyrimidine | | | |
| 59 | 2-Methylamino-4,5,6-triamino-pyrimidine | m-Aminophenol | dark purple | dark violet |
| 60 | 2-Methylamino-4,5,6-triamino-pyrimidine | Resorcinol | grayish red | brownish violet |
| 61 | 2-Methylamino-4,5,6-triamino-pyrimidine | 2,4-Diaminoanisole | dark green | dark green |
| 62 | 2-Methylamino-4,5,6-triamino-pyrimidine | m-Diaminotoluene | yellow | yellow |
| 63 | 2-Methylamino-4,5,6-triamino-pyrimidine | 3-Amino-1-phenyl-pyrazolone-5 | brownish red | brownish red |
| 64 | 6-Morpholino-2,4,5-triamino-pyrimidine | m-Phenylenediamine | olive brown | olive brown |
| 65 | 6-Morpholino-2,4,5-triamino-pyrimidine | 2,4-Diaminoanisole | grayish green | olive |
| 66 | 6-Morpholino-2,4,5-triamino-pyrimidine | m-Diaminotoluene | golden yellow | brass yellow |
| 67 | 6-Morpholino-2,4,5-triamino-pyrimidine | m-Aminophenol | grayish ruby | grayish red |
| 68 | 6-Morpholino-2,4,5-triamino-pyrimidine | Resorcinol | brownish red | brownish red |
| 69 | 6-Morpholino-2,4,5-triamino-pyrimidine | 3-Amino-1-phenyl-pyrazolone-5 | dull red | dull red |
| 70 | 6-Piperidino-2,4,5-Triamino-pyrimidine | m-Phenylenediamine | bamboo yellow | grayish yellow |
| 71 | 6-Piperidino-2,4,5-Triamino-pyrimidine | 2,4-Diaminoanisole | olive brown | olive |
| 72 | 6-Piperidino-2,4,5-Triamino-pyrimidine | m-Aminophenol | olive brown | bamboo yellow |
| 73 | 6-Piperidino-2,4,5-Triamino-pyrimidine | Resorcinol | grayish red | ivory |
| 74 | 6-Piperidino-2,4,5-Triamino-pyrimidine | m-Diaminotoluene | grayish yellow | olive brown |
| 75 | 6-Piperidino-2,4,6-Triamino-pyrimidine | 3-Amino-1-phenyl-pyrazolone-5 | chamois yellow | straw yellow |
| 76 | 6-(Di-n-propylamino)-2,4,5-triamino-pyrimidine | m-Phenylenediamine | honey yellow | olive |
| 77 | 6-(Di-n-propylamino)-2,4,5-triamino-pyrimidine | 2,4-Diaminoanisole | olive green | olive |
| 78 | 6-(Di-n-propylamino)-2,4,5-triamino-pyrimidine | m-Diaminotoluene | honey yellow | honey yellow |
| 79 | 6-(Di-n-propylamino)-2,4,5-triamino-pyrimidine | m-Aminophenol | grayish ruby | grayish ruby |
| 80 | 6-(Di-n-propylamino)-2,4,5-triamino-pyrimidine | Resorcinol | brownish red | brownish red |
| 81 | 6-(Di-n-propylamino)-2,4,5-triamino-pyrimidine | 3-Amino-1-phenyl-pyrazolone-5- | reddish brown | reddish brown |
| 82 | 5-Amino-2,4,6-tris-(methylamino)-pyrimidine | m-Phenylenediamine | oak brown | olive |
| 83 | 5-Amino-2,4,6-tris-(methylamino)-pyrimidine | 2,4-Diaminoanisole | olive | beaver brown |
| 84 | 5-Amino-2,4,6- | m-diaminotoluene | brass | olive |

TABLE 1-continued

| Example | Developer | Coupler | Shade obtained With Atmospheric $O_2$ | Shade obtained with 1% $H_2O_2$ |
|---|---|---|---|---|
| | tris-(methylamino)-pyrimidine | | yellow | |
| 85 | 5-Amino-2,4,6-tris-(methylamino)-pyrimidine | m-Aminophenol | dark ruby | brown |
| 86 | 5-Amino-2,4,6-tris-(methylamino)-pyrimidine | Resorcinol | grayish red | dull red |
| 87 | 5-Amino-2,4,6-tris-(methylamino)-pyrimidine | 3-Amino-1-phenyl pyrazolone-5 | reddish brown | light brown |
| 88 | 2-Dimethylamino-4,5,6-Triamino-pyrimidine | 3-(Diethylamino)-phenol | blue black | blue black |
| 89 | 2-Dimethylamino-4,5,6-Triamino-pyrimidine | 3-[(β-Hydroxyethyl)-amino]-phenol | blue black | blue black |
| 90 | 2-Dimethylamino-4,5,6-Triamino-pyrimidine | 3-[2-(Diethylamino)-ethyl-amino]-phenol | blue black | blue black |
| 91 | 2-Dimethylamino-4,5,6-Triamino-pyrimidine | 3-Morpholino-phenol | dark violet | dark violet |
| 92 | 2-Dimethylamino-4,5,6-Triamino-pyrimidine | 3-(Ethylpropylamino) phenol | blue black | blue black |
| 93 | 2-Dimethylamino-4,5,6-Triamino-pyrimidine | 3-(Butylamino)-phenol | blue black | blue black |
| 94 | 2-Dimethylamino-4,5,6-Triamino-pyrimidine | 3-(Ethylamino)-phenol | blue black | blue black |
| 95 | 2-Dimethylamino-4,5,6-Triamino-pyrimidine | 3-(Octylamino)-phenol | dark violet | dark violet |
| 96 | 2-Dimethylamino-4,5,6-Triamino-pyrimidine | 3-Pyrrolidino-phenol | blue black | blue black |
| 97 | 2-Dimethylamino-4,5,6-Triamino-pyrimidine | 3-Piperidino-phenol | dark blue | dark blue |
| 98 | 2-Dimethylamino-4,5,6-Triamino-pyrimidine | 3-(Dimethylamino)-phenol | dark blue | dark blue |
| 99 | 2-Dimethylamino-4,5,6-Triamino-pyrimidine | 5-(Ethylamino)-2-methyl-phenol | bluish gray | bluish gray |
| 100 | 2-Dimethylamino-amino)-phenol pyrimidine | 2-Chloro-5-(dimethyl-amion)-phenol | dark violet | dark violet |
| 101 | 2-Dimethylamino-4,5,6-Triamino-pyrimidine | 3-Hydroxydiphenyl-amine | dark blue | dark blue |
| 102 | 2-Dimethylamino-4,5,6-Triamino-pyrimidine | 3-(Methylenecyana-mido)-phenol | dark violet | dark violet |
| 103 | 2-Dimethylamino-4,5,6-Triamino-pyrimidine | 2-bromo-5-(methylene-cyanamido)-phenol | blue black | blue black |
| 104 | 2-Dimethylamino-4,5,6-Triamino-pyrimidine | 3-Tihoureido-phenol | brownish gray | dull violet |
| 105 | 2-Dimethylamino-4,5,6-Triamino-pyrimidine | 3-(Diethylamino)-4-methoxy-phenol | dark blue | dark blue |
| 106 | 2-Dimethylamino-4,5,6-Triamino-pyrimidine | 5-(Diethylamino)-2-methyl-phenol | dark blue | dark blue |
| 107 | 2-Morpholino-4,5,6-triamino-pyrimidine | m-Dimethylamino-phenol | dark blue | dark blue |
| 108 | 2-Morpholino-4,5,6-triamino-pyrimidine | 3-Hydroxydiphenyl-amine | dark blue | dark blue |
| 109 | 2-Morpholino-4,5,6-triamino-pyrimidine | 3-(Octylamino)-phenol | dark violet | violet blue |
| 110 | 2-Piperidino- | m-(Dimethylamino)- | dark | dark |

TABLE 1-continued

| Example | Developer | Coupler | Shade obtained With Atmospheric $O_2$ | Shade obtained with 1% $H_2O_2$ |
|---|---|---|---|---|
| | 4,5,6-triamino-pyrimidine | phenol | blue | blue |
| 111 | 2-Piperidino-4,5,6-triamino-pyrimidine | m-(Octylamino)-phenol | blue violet | blue violet |
| 112 | 2-Piperidino-4,5,6-triamino-pyrimidine | 3-Hydroxydiphenyl-amine | dark blue | dark blue |
| 113 | 2-Methylamino-4,5,6-triamino-pyrimidine | 3-Hydroxydiphenyl-amine | violet blue | blue violet |
| 114 | 2-Methylamino-4,5,6-triamino-pyrimidine | 3-(Octylamino)-phenol | deep violet | deep violet |
| 115 | 2-Methylamino-4,5,6-triamino-pyrimidine | m-(Dimethylamino)-phenol | deep violet | violet blue |
| 116 | 2,4,5,6-Tetraamino-pyrimidine | m-(Dimethylamino)-phenol | dark violet | dark violet |
| 117 | 2,4,5,6-Tetraamino-pyrimidine | m-(Diethylamino)-phenol | dark violet | dark violet |
| 118 | 2,4,5,6-Tetraamino-pyrimidine | m-(Ethylamino)-phenol | indigo blue | indigo blue |
| 119 | 2,4,5,6-Tetraamino-pyrimidine | m-(Ethylpropylamino)-phenol | dark violet | dark violet |
| 120 | 2,4,5,6-Tetraamino-pyrimidine | m-[(β-Hydroxyethyl)-amino]-phenol | dark violet | dark violet |
| 121 | 2,4,5,6-Tetraamino-pyrimidine | m-Piperidino-phenol | light violet | light violet |
| 122 | 2,4,5,6-Tetraamino-pyrimidine | m-Pyrrolidino-phenol | violet | violet |
| 123 | 2,4,5,6-Tetraamino-pyrimidine | 3-Hydroxydiphenyl-amine | indigo blue | indigo blue |

The following tests were conducted to determine the toxicological and dermatological properties of tetraaminopyrimidines. The test compound used was 2-dimethylamino-4,5,6-triamino-pyrimidine sulfate which was compared with known compounds, p-phenylenediamine and p-toluylenediamine sulfate. The following results were obtained.

EXAMPLE 124

Acute Toxicity

Male white mice of the CF/W 68-strain were used for the tests of general tolerance. The average weight of the test animals was 22 gm. The substances to be tested were administered by means of a stomach tube, whereby increasing dosages were used once. Ten mice were employed per dose. The volume of application was constant and was 0.2 $cm^3$/10 gm body weight. The animals were observed for a period of eight days. After the test results had been calculated according to the method of Litchfield-Wilcoxon, J. Pharm. Exptl. Ther. 96, 99–108(1949), the following $LD_{50}$-values were obtained.

| | |
|---|---|
| 2-dimethylamino-4,5,6-triamino-pyrimidine sulfate | 555 mg/kg |
| p-Phenylendiamine | 87 mg/kg |
| p-Diaminotoluene Sulfate | 110 mg/kg |

Distilled water was used as the solvent.

EXAMPLE 125

Dermal Tolerance Tests of the Hairless Mouse

Groups of five animals were used for each preparation. Small quantities of the substances to be tested were applied in form of an aqueous 5% solution to the dorsal skin of each animal. A single daily application was continued for 14 days. During this period, and at the end of the test, none of the animals showed any reaction.

EXAMPLE 126

Mucocutaneous Tolerance of the Rabbit Eye

Groups of albino rabbits were employed for these tests of the local tolerance. Small quantities of the substances to be tested were employed as aqueous 5% preparations; and were once dripped into the conjunctival sac of one eye of each rabbit. The reactions of the mucous membranes of the eye were evaluated according to the point system of Draize, [Appraisal of the Safety of Chemicals in Foods, Drugs and Cosmetics. Assoc. of Food and Drug Officials of the U.S., pp. 49–52 (1959)]. This evaluation which was made 2, 6, 24 and 48 hours after the application and it showed that p-phenylenediamines leads to a low-grade redness and exudation of the conjuctiva which could not be detected 24 hours after the dripping in. The other two test compounds were tolerated without reaction.

EXAMPLE 127

Skin (Tissue) Tolerance Test of White Mice after a Single Intracutaneous Application of Various Concentrations of the Preparations to be Tested This test of local tolerance was conducted according to Barail, [J. Society Cosmetic Chemists 11, 241 (1960)]. In this test, small quantities of the compounds to be tested were transcutaneously applied to the abdominal skin of white mice, whereby increasing concentration were used. After 24 hours, the test animals were sacrificed and the treated places of the skin were cut out and dried. The skin damages were evaluated according to a point system, in which the blood irrigation and other damages of the treated skin are taken into account. In this test, a larger animal group of ten mice was employed per preparation and per test concentration. Hence, finer differences with respect to local tolerance could be observed according to the above-described test procedure. The test results are reported in the following Table II.

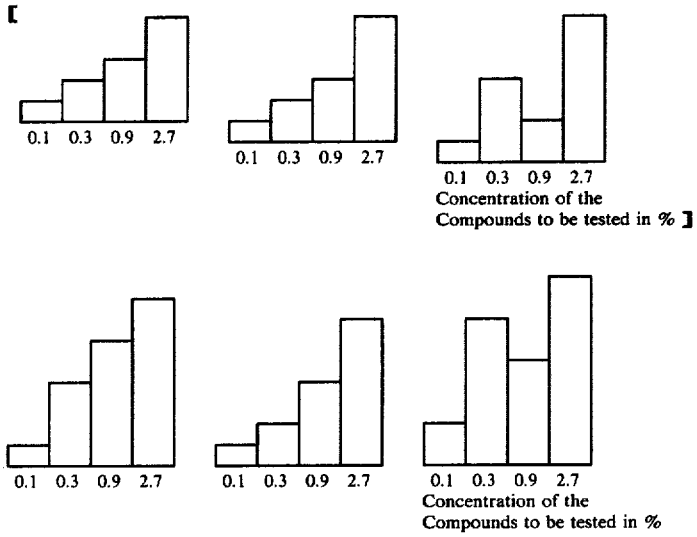

It is evident from the above test results that (2-dimethylamino)-4,5,6-triamino-pyrimidine sulfate shows the best results of the tested developers with respect to general and local tolerance. Besides these good toxicological and dermatological properties, the tetraaminopyrimidines used [into] *in* the hair coloring preparations according to the invention have the additional advantages that the color can readily be developed with atmospheric oxygen. These hair coloring preparations produce an extraordinary variation of shades which are distinguished by excellent fastness to light and washing, as well as by excellent resistance to abrasion, and they can easily be removed with reducing agents.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

We claim:

1. An aqueous preparation for the dyeing of hair consisting essentially of (1) from 0.2% to 5% by weight of an oxidation dyestuff combination of a developer component, and a coupling component in substantially equimolar amounts, said developer component consisting essentially of (A) a tetraaminopyrimidine of the formula

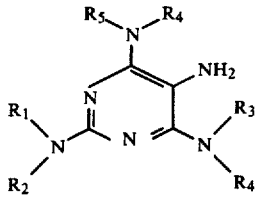

wherein $R_1$, $R_2$, $R_3$, $R_4$, $R_5$ and $R_6$ are each selected from the group consisting of hydrogen, phenyl, 6-alkyl having 1 to 4 carbon atoms, phenylalkyl having 7 to 10 carbon atoms, phenylalkenyl having 7 to 10 carbon atoms, $$X—(CH_2)_n—$$

wherein n is an integer from 1 to 4, and X is selected from the group consisting of hydroxyl, halogen and $NR_7R_8$— in which $R_7$ and $R_8$ are selected from the group consisting of hydrogen and alkyl having 1 to 4 carbon atoms, and together with the nitrogen atom $R_7$ to $R_8$ form a 5 to 6 membered heterocyclic ring optionally containing an additional nitrogen atom or an oxygen atom, and wherein $R_1$ and $R_2$ or $R_3$ and $R_4$ or $R_5$ and $R_6$, together with the nitrogen atom form a 5 to 6 membered heterocyclic ring, optionally containing another nitrogen or oxygen atom in the ring or (B) a water-soluble acid addition salt of (A); (2) from 0% to 5% by weight of a direct dyestuff; (3) from 0% to 30% by weight of a surfactant; (4) from 0% to 25% by weight of a thickener; and (5) the balance up to 100% by weight of water.

2. The aqueous preparation of claim 1, wherein $R_1$, $R_2$, $R_3$, $R_4$, $R_5$ and $R_6$ are each selected from the group consisting of hydrogen, methyl, ethyl, isopropyl, n-propyl, butyl, phenyl, benzyl, benzylidene; and $—(CH_2)_n—X$ wherein $R_1$ and $R_2$ or $R_3$ and $R_4$, or $R_5$ and $R_6$, together with the nitrogen atom form a substituent selected from the group consisting of piperidino and morpholino; and wherein n is 1,2 or 3 and X is selected from the group consisting of hydroxyl, halogen and $—NR_7R_8$ in which $R_7$ and $R_8$ are selected from the group consisting of hydrogen and alkyl having 1 to 4 carbon atoms.

3. The aqueous preparation of claim 1, wherein said coupling component is selected from the group consisting of (a) a 1-phenyl-pyrazol-5-one, (b) an aromatic amine (c) an aromatic alcohol, and (d) a pyrazolidinedione.

4. The aqueous preparation of claim 1, wherein there is from 1% to 3% by weight of said oxidation dyestuff combination.

5. The aqueous preparation of claim 1, wherein the developer component is selected from the group consisting of (A) 2,4,5,6-tetraamino-pyrimidine, 4-dimethylamino-2,5,6-triaminopyrimidine, 2-dimethylamino-4,5,6-triamino-pyrimidine, 2-piperidino-4,5,6-triamino-pyrimidine, 2-morpholino-4,5,6-triamino-pyrimidine, 6-morpholino-2,4,5-triamino-pyrimidine, 6-piperidino-2,4,5-triamino-pyrimidine, 6-(di-n-propylamino)-2,4,5-triamino-pyrimidine, 5-amino-2,4,6-tris-(methylamino)-pyrimidine and 2-methylamino-4,5,6-triamino-pyrimidine and (B) a water soluble acid addition salt of (A).

6. The aqueous preparation of claim 1, wherein said coupling component is selected from the group consisting of (a) a m-aminophenol of the formula

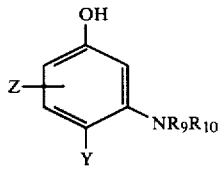

wherein Z and Y are each selected from the group consisting of hydrogen, halogen, hydroxyl, amino, alkyl having 1 to 4 carbon atoms, alkoxy having 1 to 4 carbon atoms, alkylamino having 1 to 4 carbon atoms, dialkylamino having 1 to 4 carbon atoms in each of the alkyls;

wherein $R_9$ is selected from the group consisting of alkyl having 1 to 10 carbon atoms, hydroxyalkyl having 1 to 10 carbon atoms, phenyl, anilino, hydroxyphenyl, benzyl, methylenecyanamido, propionamido, ureido, thioureido, oxalyl ester of an alcohol having 1 to 4 carbon atoms, $M—(CH_2)_m—$ wherein m is an integer from 1 to 4 and M is selected from the group consisting of hydroxyl, halogen, and $—NR_{11}R_{12}$, in which $R_{11}$ and $R_{12}$ are selected from the group consisting of hydrogen and alkyl having 1 to 4 carbon atoms and wherein $R_{10}$ is selected from the group consisting of hydrogen and $R_9$, wherein $R_9$ and $R_{10}$ can together with the nitrogen atom form a five to six membered heterocyclic ring optionally containing an additional nitrogen atom or an oxygen atom and b. a water-soluble acid addition salt of (a).

7. The aqueous preparation of claim 6, wherein Z and Y are each selected from the group consisting of hydrogen, methyl, methoxy, amino, chloro and hydroxyl;

wherein $R_9$ is selected from the group consisting of methyl, ethyl, octyl, propyl, hydroxyethyl, phenyl, benzyl, anilino, hydroxyphenol, ureido, thioureido, methylenecyanamido and diethylaminoethyl, wherein $R_{10}$ is selected from the group consisting of hydrogen and $R_9$, and wherein $R_9$ and $R_{10}$ together with the nitrogen atom form a member selected from the group consisting of pyrrolidino, morpholino, and piperidino.

8. A process for the dyeing of human hair comprising applying to said hair at temperatures ranging substantially from 15° C. to 40° C. for a time sufficient to effect dyeing, an effective amount of the aqueous preparation of claim 1.

9. The process for the dyeing of human hair of claim 8, wherein said preparation also contains a chemical oxidizing agent.

* * * * *

UNITED STATES PATENT AND TRADEMARK OFFICE

CERTIFICATE OF CORRECTION

PATENT NO. : 30199 Reissue

DATED : January 29, 1980

INVENTOR(S) : DAVID ROSE, FERDI SAYGIN, ERWIN WEINRICH

It is certified that error appears in the above—identified patent and that said Letters Patent is hereby corrected as shown below:

Column 3, line 8: Before "hydroxyl" insert the following: -- piperidino and morpholino; and wherein n is 1, 2 or 3 and is selected from the group consisting of --.

Column 14, line 5: "as"should read -- was --.

Column 21/22, Table 1, Example 100, under the column "Coupler": "amion)-phenol" should read -- amino)-phenol --.

Column 25: The Table II which reads

"

[

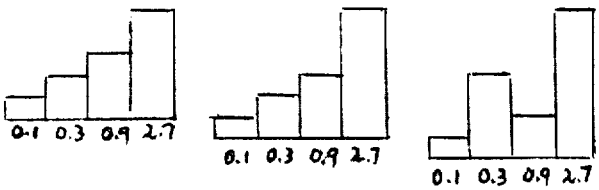

Concentration of the Compounds to be tested in % ]

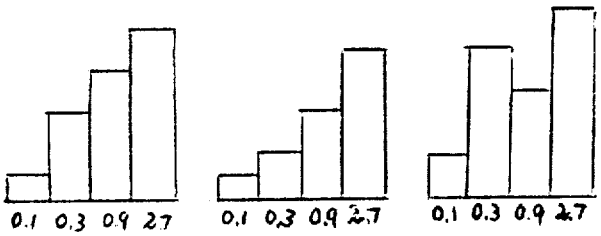

Concentration of the Compounds to be tested in % "

UNITED STATES PATENT AND TRADEMARK OFFICE

CERTIFICATE OF CORRECTION

PATENT NO. : 30,199 Reissue

DATED : January 29, 1980

INVENTOR(S) : DAVID ROSE, FERDI SAYGIN, ERWIN WEINRICH

It is certified that error appears in the above—identified patent and that said Letters Patent is hereby corrected as shown below:

should read:

--

TABLE II

| | Skin (Tissue) Test of White Mice after Intracutaneous Application (Test according to Barail) Average Values after Evaluation of 10 Animals Employed Each Time per Concentration | | |
|---|---|---|---|
| Points or Degree of Skin Damage | 4,5,6-Triamino-2-(Dimethylamino)-pyrimidine Sulfate | p-Phenylenediamine | p-Diamino-toluene Sulfate |

[

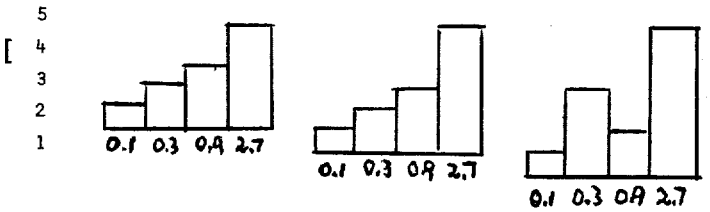

Concentration of the Compounds to be tested in % ]

UNITED STATES PATENT AND TRADEMARK OFFICE

CERTIFICATE OF CORRECTION

PATENT NO. : 30,199 Reissue

DATED : January 29, 1980

INVENTOR(S) : DAVID ROSE, FERDI SAYGIN, ERWIN WEINRICH

It is certified that error appears in the above—identified patent and that said Letters Patent is hereby corrected as shown below:

TABLE II continued:

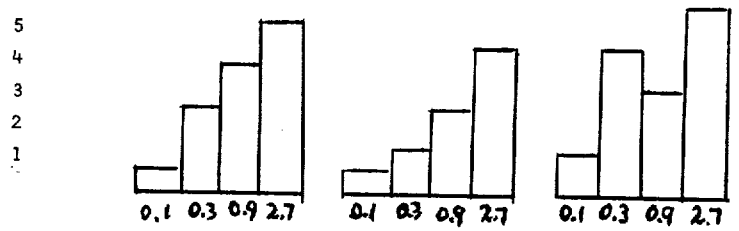

Concentration of the Compounds to be tested in % --.

Signed and Sealed this

Seventh Day of July 1981

[SEAL]

Attest:

RENE D. TEGTMEYER

Attesting Officer

Acting Commissioner of Patents and Trademarks